(12) United States Patent
Buyse et al.

(10) Patent No.: US 9,092,566 B2
(45) Date of Patent: Jul. 28, 2015

(54) METHODS FOR CENTRAL MONITORING OF RESEARCH TRIALS

(75) Inventors: Marc Buyse, Brussels (BE); Tomasz Burzykowski, Hasselt (BE); David Venet, Brussels (BE); Erik Doffagne, Wavre (BE)

(73) Assignee: International Drug Development Institute, Louvain-la-Neuve (BE)

( * ) Notice: Subject to any disclaimer, the term of this patent is extended or adjusted under 35 U.S.C. 154(b) by 665 days.

(21) Appl. No.: 13/452,338

(22) Filed: Apr. 20, 2012

(65) Prior Publication Data

US 2013/0282320 A1   Oct. 24, 2013

(51) Int. Cl.
G01D 18/00 (2006.01)
G06F 19/00 (2011.01)
G06Q 50/00 (2012.01)

(52) U.S. Cl.
CPC .............. *G06F 19/363* (2013.01); *G06Q 50/00* (2013.01)

(58) Field of Classification Search
USPC .......................................................... 702/85
See application file for complete search history.

(56) References Cited

U.S. PATENT DOCUMENTS

| | | | |
|---|---|---|---|
| 6,466,929 B1 | 10/2002 | Brown et al. | 706/48 |
| 6,985,846 B1 | 1/2006 | Dunlavey | 703/22 |
| 7,054,823 B1 | 5/2006 | Briegs et al. | 705/2 |
| 7,065,524 B1 | 6/2006 | Lee | 1/1 |
| 7,216,116 B1 | 5/2007 | Nilsson et al. | 1/1 |
| 7,269,517 B2 | 9/2007 | Bondarenko | 702/19 |
| 7,392,119 B2 | 6/2008 | Allard et al. | 701/33.9 |
| 8,655,817 B2 * | 2/2014 | Hasey et al. | 706/45 |
| 2002/0023083 A1 | 2/2002 | Durkalski | |
| 2002/0174115 A1 | 11/2002 | shibuya et al. | |
| 2005/0182657 A1 | 8/2005 | Abraham-Fuchs et al. | |
| 2005/0182658 A1 | 8/2005 | Abraham-Fuchs et al. | |
| 2005/0182663 A1 | 8/2005 | Abraham-Fuchs et al. | |
| 2005/0182664 A1 | 8/2005 | Abraham-Fuchs et al. | |
| 2007/0038472 A1 | 2/2007 | Finken et al. | |
| 2007/0150314 A1 | 6/2007 | Abraham-Fuchs et al. | |
| 2007/0179811 A1 | 8/2007 | Reiner | |
| 2008/0109455 A1 | 5/2008 | Katz | |

(Continued)

FOREIGN PATENT DOCUMENTS

| | | |
|---|---|---|
| EP | 881146 | 12/1998 |
| JP | 2004030143 | 1/2004 |

(Continued)

*Primary Examiner* — Tung S Lau
*Assistant Examiner* — Xiuquin Sun
(74) *Attorney, Agent, or Firm* — Locke Lord LLP; Scott D. Wofsy; Christoper J. Capelli

(57) ABSTRACT

A method for central monitoring of a research trial includes the steps of creating and storing a clinical database consisting of datasets generated during the research trial, preprocessing the database to remove variables that are unsuitable for analysis, extracting metadata from the database to identify types of the variables, storing the preprocessed datasets and corresponding metadata in a statistical database, executing statistical tests on a data collection center by data collection center basis to detect abnormalities and patterns present in datasets, creating and storing a matrix containing p-values based upon the executed statistical tests, identifying any outlying data collection centers by summarizing the p-values, determining if any of the executed statistical tests are faulty and removing such faulty executed statistical tests from the matrix to create a filtered matrix, and computing an overall p-value score.

18 Claims, 4 Drawing Sheets

(56) References Cited

U.S. PATENT DOCUMENTS

| | | |
|---|---|---|
| 2008/0114624 A1 | 5/2008 | Kitts |
| 2008/0161700 A1 | 7/2008 | Sachanandani et al. |
| 2008/0195600 A1 | 8/2008 | Deakter |
| 2008/0270420 A1 | 10/2008 | Rosenberg |
| 2008/0281826 A1 | 11/2008 | Sanders et al. |
| 2009/0043593 A1 | 2/2009 | Herbrich et al. |
| 2009/0043817 A1 | 2/2009 | Sanders et al. |
| 2010/0250273 A1 | 9/2010 | Li |

FOREIGN PATENT DOCUMENTS

| | | |
|---|---|---|
| SE | 200100606 | 8/2002 |
| WO | 9632684 | 10/1996 |
| WO | 9927444 | 6/1999 |
| WO | 0026819 | 5/2000 |
| WO | 0063793 | 10/2000 |
| WO | 0193160 | 12/2001 |
| WO | 0251354 | 7/2002 |
| WO | 0293320 | 11/2002 |
| WO | WO-04/049217 A1 | 6/2004 |
| WO | 200536446 | 4/2005 |
| WO | 200684196 | 8/2006 |
| WO | 200693645 | 9/2006 |
| WO | 200848958 | 4/2008 |
| WO | 200964817 | 5/2009 |

\* cited by examiner

Center X0013 (N=18)

| Test | Dataset | feature | pvalue | rank | details |
|---|---|---|---|---|---|
| mean | labs | hemoglobin | 0.062 | 16 | 12.2 (Rank 13) vs 13 |
| mean | labs | creatinine | 0.019 | 7 | 132 (Rank 4) vs 97 |
| mean | demog | age | 0.052 | 12 | 44 (Rank 12) vs 51 |
| mean | diagnos | size | 0.00012 | 1 | 4.64 (Rank 1) vs 2.08 |
| mean | diagnos | grade | 0.078 | 17 | 2 (Rank 24.5) vs 1.31 |
| mean | surgery | noderem | 0.083 | 25 | 17.1 (Rank 18) vs 8.01 |
| mean | surgery | nodepos | 0.003 | 1 | 4.02 (Rank 1) vs 0.195 |
| sequence outlier | labs | WBC | 0.011 | 2 | 1/173 (0.00578) vs 6.49e-05 |

Figure 4

METHODS FOR CENTRAL MONITORING OF RESEARCH TRIALS

BACKGROUND OF THE INVENTION

1. Field of the Invention

The subject disclosure relates to methods and systems for monitoring research trials via a distributed computing network, and more particularly to improved methods and systems for centrally monitoring research trials using statistical methods to verify the quality of the trials. Multi-center clinical trials of new therapies will be used throughout the disclosure as a typical, but by no means exclusive, example of such trials.

2. Background of the Related Art

Over the decade of 2001-2010, clinical research costs have sky-rocketed while new drug approvals have decreased by one third. At the current pace of increase in costs, adequately sized clinical trials may become infeasible. Alternatively, such costs will have to be reflected in the price of new drugs, which will eventually cause an intolerable burden on health care systems.

In view of typical trial costs, different options have been suggested to reduce some of these costs without compromising the scientific validity of the trials. The greatest potential savings lie in the labor-intensive activities such as on-site monitoring, which can represent as much as 30% of the total budget in large global clinical trials. It is therefore not surprising that the current practice of performing intensive on-site monitoring is coming into question. A draft guidance of the U.S. Food and Drug Administration (FDA) states unequivocally: "FDA encourages greater reliance on centralized monitoring practices than has been the case historically, with correspondingly less emphasis on on-site monitoring".

SUMMARY OF THE INVENTION

In view of the above, a need exists for a system that effectively verifies the quality of trials that utilize centralized monitoring. The improved methods and systems would greatly reduce trial costs without any reduction in effectiveness. It is an object of the technology proposed to utilize central monitoring as a cost-effective way of ensuring data quality in clinical trials.

The present disclosure is directed to a method for central monitoring of a research trial utilizing a plurality of distributed data collection centers. The method includes the steps of creating and storing a database consisting of datasets generated during the research trial, preprocessing the database to remove variables that are unsuitable for analysis, extracting metadata from the database to identify types of the variables, storing the preprocessed datasets and corresponding metadata in a statistical database that is in a format compatible for analysis, executing statistical tests on a data collection center by data collection center basis to detect abnormalities and patterns present in datasets of the statistical database, creating and storing in the network a matrix containing p-values based upon the executed statistical tests, wherein the matrix has as many rows as there are data collection centers and as many columns as executed statistical tests, determining if any of the executed statistical tests are faulty and removing such faulty executed statistical tests from the matrix to create a filtered matrix, and identifying any outlying data collection centers by computing an overall p-value score for each data collection center according to a weighted average of the p-values of the executed statistical tests, using a formula such as:

$$sc_k \exp\left(\frac{1}{qN_k} \sum_{i=1}^{qN_k} \log(p_{ik})\right)$$

where $N_k$ is the number of tests performed for center k, $p_{ik}$ are the sorted p-values for center k, and q is a user-selected value between 0 and 1.

The method also computes at least one sub-score selected from the group consisting of: (1) Tests on values: tests in this category look at distribution characteristics such as, for example, the mean or the standard deviation (proportion tests on categorical variables also fall in this category), wherein the tests on values include tests on repeated measurements for variables measured several times in the trial; (2) Tests on dates; (3) Tests on digits preference; (4) Tests on underreporting such as, for example, tests on missing values and on count of records; and (5) Multivariate tests: tests on multivariate inliers and outliers. The preprocessing step may include removing variables selected from the group consisting of: variables for which all observations are missing; variables for which all observations have the same value; variables for which the number of observations is too small; and technical variables that are irrelevant for the purposes pursued, such as a patient identifier. The extracting of metadata step may also include deriving a number of visits per patient and creating a list of patients per center.

In still another embodiment of the present disclosure, the executing statistical tests step includes comparing each center to the other centers for each variable by fitting statistical models. The method may also include the steps of deriving from the model aggregate numbers for each center. The aggregate number can be a mean, a variance or any relevant estimator of the distribution characteristic of a variable for the respective center. From the model, a probability can be assigned to each center, wherein the probability indicates a likelihood to draw a center more extreme than the corresponding center. The identifying step may analyze a Principal Component Analysis (PCA) of the p-values and a score method of the p-values.

It should be appreciated that the subject technology can be implemented and utilized in numerous ways, including without limitation as a process, an apparatus, a system, a device, a method for applications now known and later developed or a computer readable medium. These and other unique features of the methods and systems disclosed herein will become more readily apparent from the following description and the accompanying drawings.

BRIEF DESCRIPTION OF THE DRAWINGS

So that those having ordinary skill in the art to which the disclosed methods and systems appertain will more readily understand how to make and use the same, reference may be had to the following drawings.

FIG. 4 is an example table with details on statistical tests for a given data collection center in accordance with the subject disclosure.

DETAILED DESCRIPTION OF PREFERRED EMBODIMENTS

Figure 1:
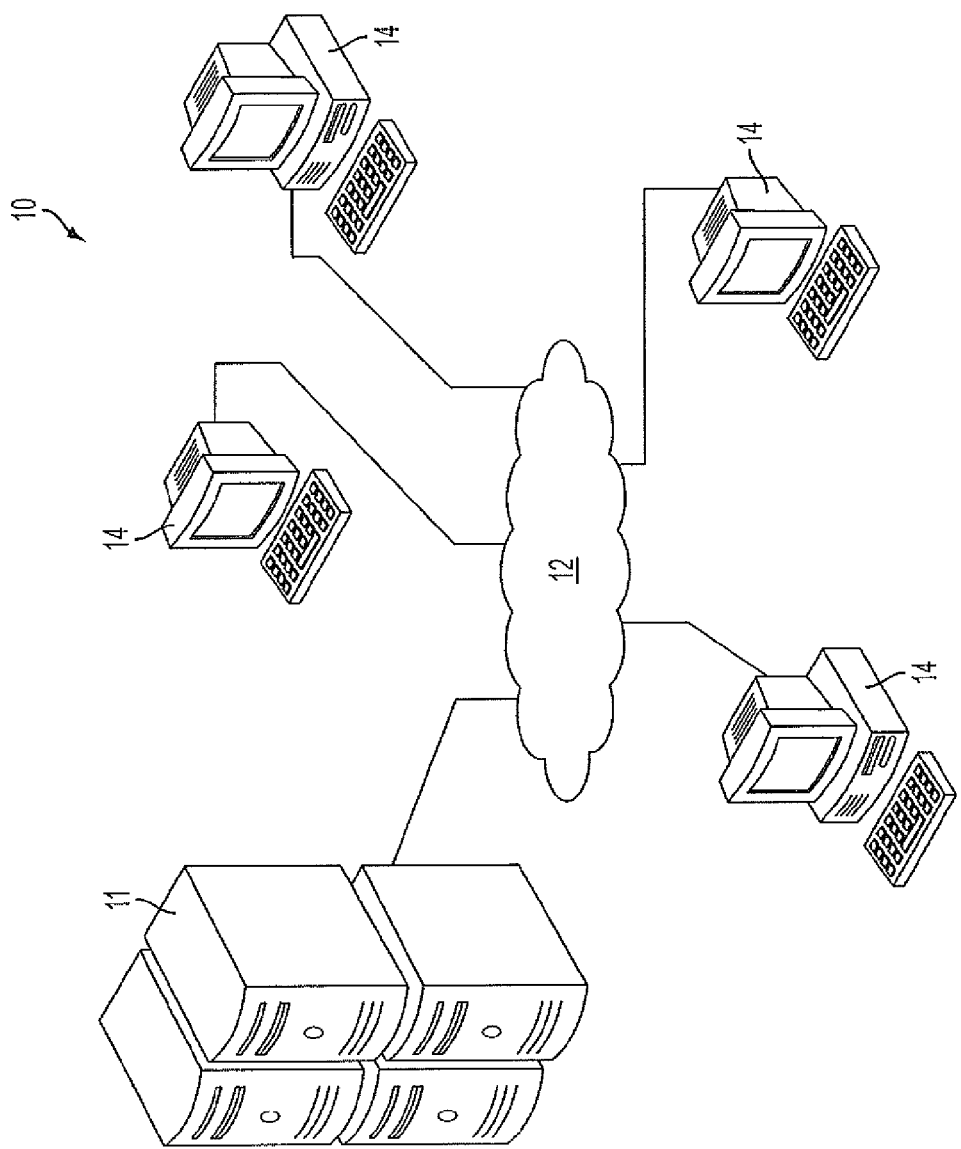
FIG. 1 is a diagram showing a distributed computing environment for utilizing centralized statistical monitoring of research trials in accordance with the subject disclosure.

The subject technology overcomes many of the prior art problems associated with research trials that collect large volumes of data and need to have the data be verifiable in a cost-effective manner. The advantages, and other features of the methods and systems disclosed herein, will become more readily apparent to those having ordinary skill in the art from the following detailed description of certain preferred embodiments taken in conjunction with the drawings which set forth representative embodiments of the present invention and wherein like reference numerals identify similar structural elements.

Clinical trial sponsors are required to set up appropriate measures to monitor the conduct of their trials. One of the aims of monitoring is to ensure data accuracy and completeness. The most common method used to verify data quality is through Source Data Verification (SDV) during on-site monitoring visits. SDV consists of comparing information recorded in the Case Report Form (CRF) with the corresponding source documents. Such manual verification is extremely costly, and its contribution to data quality has been questioned.

Extensive monitoring with 100% SDV is undesirable, even in regulatory trials, and reduced monitoring, which consists of controlling only a random sample of data, is much more cost-effective. The random sampling of reduced monitoring can be performed at various levels: country; centers within countries; patients within centers; visits within patients; CRF pages within visits; and the like.

Reduced monitoring may be adapted to the risk associated with the experimental procedure. For example, a trial involving innocuous procedures or well-known treatments could involve less monitoring than a trial involving invasive procedures or experimental new drugs. Another option is "targeted" monitoring, (also known as "adaptive" or "triggered" monitoring), where the intensity and frequency of on-site monitoring is triggered by key performance or risk indicators. These indicators typically focus on critical aspects of trial conduct such as: accrual performance (e.g., actual accrual rate compared with projected accrual rate, accrual patterns over time); protocol adherence (e.g., percentage of protocol deviations, percentage of dropouts); treatment compliance (e.g., percentage of dose reductions or delays); safety reporting (e.g., percentage of adverse events and serious adverse events reported); and data management (e.g., percentage of overdue forms, query rate, query resolution time).

On-site monitoring is useful to prevent or detect procedural errors in the trial conduct at data collection centers. Central statistical monitoring is useful to detect data errors, whether due to faulty equipments, negligence or fraud. Central monitoring can be based on key performance or risk indicators, or on statistical methods.

The following describes using statistical methods to conduct central monitoring. Central statistical monitoring utilizes the highly structured nature of clinical data, since the same protocol is implemented identically in all data collection centers, using the same CRF. Hence the same hierarchical data structure is used throughout the trial, with variables or items grouped by CRF page (or screen when electronic data capture is used), CRF pages or screens grouped by visit, visits grouped by patient, patients grouped by investigator, investigators grouped by center, centers grouped by country, and countries grouped by geographical area or continent.

When the trial is randomized, the group allocated by randomization provides another design variable that allows for specific statistical tests to be performed, because baseline variables are not expected to differ between the randomized groups (but through the play of chance), while outcome variables are expected to differ about equally in all centers (but through the play of chance) if the treatments under investigation have a true effect. Abnormal trends and patterns in the data can be detected by comparing the distribution of all variables in each center against all other centers. Such comparisons can be performed either one variable at a time in a univariate fashion or with several variables, taking into account the multivariate structure of the data, or using longitudinal data when the variable is repeatedly measured over time.

Statistical data checks are especially useful because the multivariate structure and/or time dependence of variables are very sensitive to deviations in the case of errors and hard to mimic in the case of fraud. Fabricated or falsified data, even if plausible univariately, are likely to exhibit abnormal multivariate patterns that are detectable statistically. In addition, humans are poor random number generators, and are generally forgetful of natural constraints in the data; hence tests on randomness of the data can detect invented data. Every piece of information collected in the CRF during the conduct of the trial, and every variable coded in the clinical database is potentially indicative of data quality, not just those associated with a set of indicators predefined to reflect site performance in terms of data quality ("key risk indicators"). A statistical approach therefore requires a large number of statistical tests to be performed. These tests generate a high-dimensional matrix of p-values representing the probability to draw a center more extreme than the center observed, which can be analyzed by statistical methods and bio-informatics tools to identify outlying centers. The matrix has as many rows as there are data collection centers and as many columns as executed statistical tests.

Referring now to the FIG. 1, there is shown a block diagram of an environment 10 with central monitoring of research trials embodying and implementing the methodology of the present disclosure. The present technology allows users, who gather data from trial participants, to enter data. The following discussion describes the structure of such an environment 10 but further discussion of the applications programs and data that embody the methodology of the present invention is described elsewhere herein.

The environment 10 includes one or more servers 11 which communicate with a distributed computer network 12 via communication channels, whether wired or wireless, as is well known to those of ordinary skill in the pertinent art. In a preferred embodiment, the distributed computer network 12 is the Internet. For simplicity, although a plurality of servers 11 are shown, the term server 11 applies well to the grouping as such computing power is well-known to be aggregated. Server 11 hosts multiple Web sites and houses multiple databases necessary for the proper operation of the central monitoring methods in accordance with the subject invention.

The server 11 is any of a number of servers known to those skilled in the art that are intended to be operably connected to a network so as to operably link to a plurality of clients or user computers 14 via the distributed computer network 12. The plurality of computers or clients 14 may be desktop computers, laptop computers, personal digital assistants, tablet computers, scanner devices, cellular telephones and the like. The clients 14 allow users to enter and access information on the server 11. For simplicity, only four clients 14, 16 are shown but the number is unlimited. The clients 14 have displays and an input device(s) as would be appreciated by those of ordinary skill in the pertinent art.

The flow charts herein illustrate the structure or the logic of the present technology, possibly as embodied in computer program software for execution on a computer, digital processor or microprocessor in the environment 10. Those skilled in the art will appreciate that the flow charts illustrate the structures of the computer program code elements, including logic circuits on an integrated circuit, that function according to the present technology. As such, the present technology may be practiced by a machine component that renders the program code elements in a form that instructs a digital processing apparatus (e.g., computer) to perform a sequence of functional steps similar to or corresponding to those shown in the flow charts.

Figure 2:
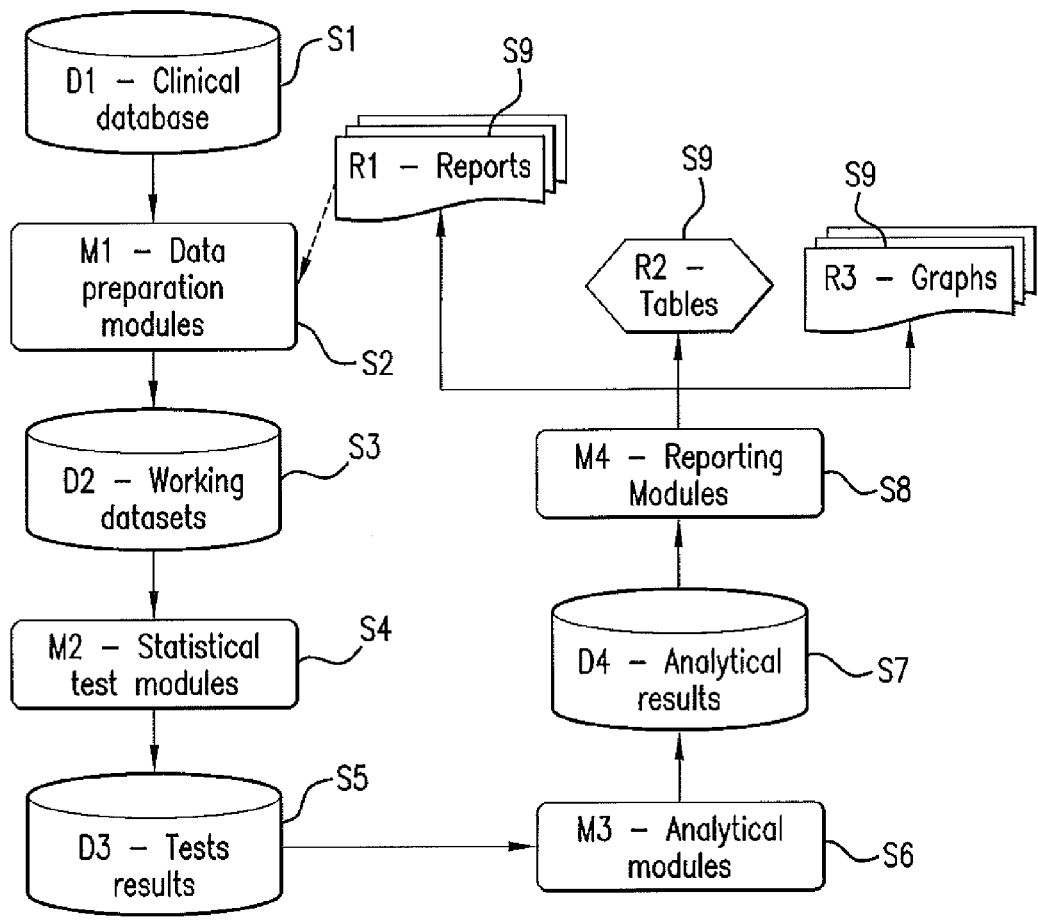
FIG. 2 is a flow diagram of a process performed by the central monitoring system of FIG. 1.

Referring now to FIG. 2, there is illustrated a flowchart depicting a process for facilitating the central monitoring methods in accordance with an embodiment of the present technology. In a preferred embodiment, a company (not shown) hosts a Web site to provide access for research trial practitioners to utilize the environment 10 for central monitoring.

The environment 10 also provides for administration and security maintenance. Therefore, although each user (e.g., data managers, statisticians, monitors, sponsors, etc.) of the subject technology has access to a user interface on a client 14, each group's access is controlled. The interface specifies which aspects of the program can be accessed, and at what level in order to maintain compliance with technical electronic data interchange standards and legal confidentiality restraints such as HIPAA (Health Insurance Portability and Accountability Act) and quality standards such as GCP (Good Clinical Practice), if the invention is used to monitor clinical trials of new drugs, biologicals or medical devices. Such limitations of functionality are well known to those skilled in the art and therefore not further described herein.

The flowchart of FIG. 2 also includes portions of the architecture to support the successive processing steps of the subject methodology. The architecture include three types of system components or architecture where business logic modules are denoted the letter "M", data components are denoted by the letter "D", and results are denoted by the letter "R" to help more clearly illustrate how the various components operate and interact.

At step S1, a database D1 is created and stored for use in the central monitoring method or process. In clinical trials, the database is typically provided by the sponsor of the trial as a snapshot of the clinical database in SAS® format. In such cases, the clinical database D1 consists of a set of SAS® data files in SAS7BDAT format. The clinical data are scattered in several datasets that relate to portions of the CRF or other grouping criterion. The term "dataset" stands for data in tabular form where the columns correspond to the variables and the rows to the observations.

At step S2, a data preparation module M1 imports the clinical database D1 and performs preprocessing, extracts metadata, and creates working datasets D2, which are stored at step S3. In one embodiment, the user specifies the subject identifier, center identifier, visit number and some other parameters like the name of technical variables that are removed.

The preprocessing in step S2 consists of the removal of variables that are not suitable for the analysis. It may be variables for which all observations are missing, for which all observations have the same value, for which the number of observations is too small (less than 5 patients) or variables that have been explicitly specified by the user as not relevant (i.e. technical variables).

The extraction of metadata in step S2 includes the derivation of number of visits per patient, creation of the list of patients per center. Metadata are created to identify the type of each variable, duplicate variables (e.g. same variable available coded as character and as numeric), and variables that are replicated (information that is collected more than once per patient).

At step S3, the working datasets D2 consists to a collection of preprocessed datasets and the associated metadata obtained from S2. The working datasets are stored in a format compatible with the statistical test modules M2 performed in step S4.

The statistical test modules M2 then perform step S4 of executing statistical tests. The role of the statistical tests is to detect abnormalities and patterns present in the datasets and more globally to assess the overall data quality and center performance. Each statistical test compares each center to the other centers, for each variable. Preferably, all statistical tests conceptually follow the same pattern of calculating an aggregate number for each center (e.g., the mean or standard deviation of a variable). Each center is then compared to all other centers using the aggregate numbers. A probability can be given to each center, which is the probability to draw a center more extreme than the center observed. A different statistical model is fitted for each variable, so that the variable's distributional properties (e.g., variance) are properly taken into account.

As part of step S5, the results from the statistical test modules M3 are stored in a Test Results database D3. The results consist of a matrix containing the p-values. The p-value matrix has as many rows as there are centers and as many columns as tests performed. Additional information is kept such as aggregate numbers used for the statistical tests and information on the statistical models used (i.e., model fitted, estimated parameters, etc).

Figure 5:
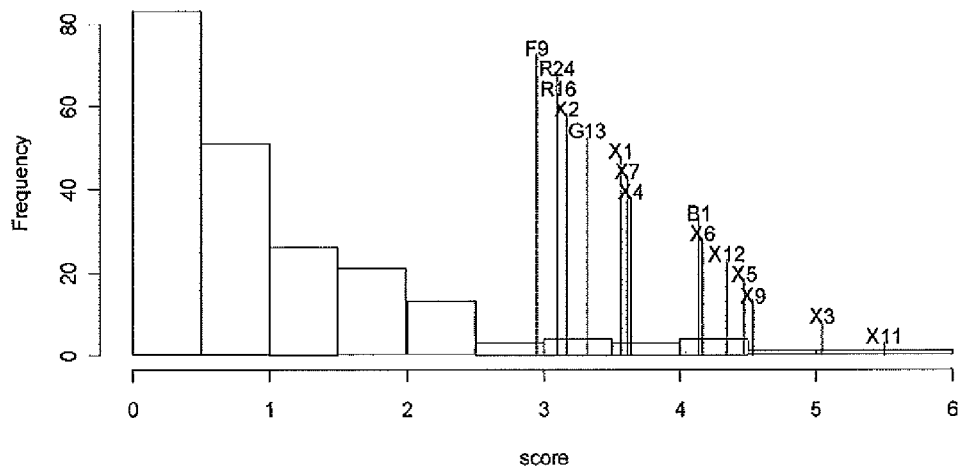
FIG. 5 is an example of a graphical output generated by the central monitoring system in accordance with the subject disclosure.
Figure 6:
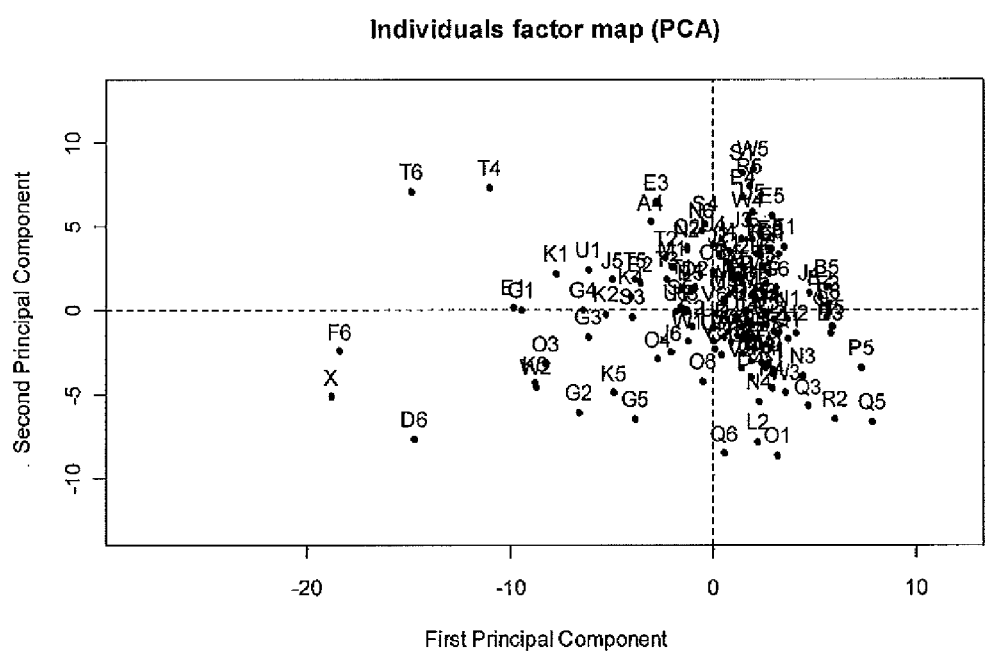
FIG. 6 is an example of an individual factor map obtained from the Principal Component Analysis (PCA) in accordance with the subject technology.

At step S6, the analytical module M3 processed the test results stored in the Test Results database D3. The analytical module M3 summarizes the large amount of p-values that have been generated by the statistical test module M2 in order to identify outlying centers. In one embodiment, two techniques are both implemented to perform the center ranking: a Principal Component Analysis (PCA); and a score method described below. Both of these methods utilize the tests result matrix obtained from M2. The two methods are complementary and provide different graphical representations of the results, as shown in FIGS. 5 and 6. The method for calculating the scores is described below.

The PCA method implemented by the analytical module M3 consists of four steps. First, tests with missing results beyond a predetermined threshold are excluded. In one embodiment, to exclude such tests, columns of the matrix for which there is more than a given percentage m % such as 30% of missing results are excluded. Second, p-values below a given threshold t such as $10^{-10}$ are set to the threshold. Third, the logarithm (base 10) of p-values is computed. Fourth, PCA is performed. The results of the PCA are stored in D4 Analytical Database in step S7.

The scoring implemented in the analytical module M3 starts by removing the non-informative tests, then the p-value matrix is preprocessed and finally the p-value score is computed.

The removal of non informative tests improves the performance of the present invention by reducing the amount of noise. The non-informative tests can grouped in three categories. The first category is tests with too many missing p-values. Tests for which the proportion of missing p-values exceeds the threshold of m % are removed. The second category is tests with too many significant results: Tests that have more than a given percentage such as 10% of p-values below $10^{-2}$ are excluded. The third category the tests with too few significant results: Tests that have no p-value below the minimal p-value expected after Bonferroni correction are excluded.

The preprocessing step is aimed to avoid overweighting the analysis by extreme p-values. All p-values smaller than a given threshold t such as $10^{-10}$ are set to the threshold.

The different statistical tests look at different characteristics of the data. Considering all tests together gives more weight to tests that have been performed more frequently than others. To avoid this problem, five categories of tests have been defined: (1) Tests on values: tests in this category look at distribution characteristics such as, for example, the mean or the standard deviation (proportion tests on categorical variables also fall in this category), wherein the tests on values include tests on repeated measurements for variables measured several times in the trial; (2) Tests on dates; (3) Tests on digits preference; (4) Tests on underreporting such as, for example, tests on missing values and on count of records; and (5) Multivariate tests: tests on multivariate inliers and outliers.

Six scores are computed: one overall p-value score; and five sub-scores (one for each category of tests described above). The p-value score $sc_k$ for the center k is computed as a weighted average of the p-values of the executed statistical tests, using a formula such as:

$$sc_k \exp\left(\frac{1}{qN_k}\sum_{i=1}^{qN_k} \log(p_{ik})\right)$$

where $N_k$ is the number of tests performed for center k, $p_{ik}$ are the sorted p-values for center k, and q is a value between 0 and 1. The role of the quantile q is to perform the calculation only on the most significant p-values. It is useful to specify q<1 when the number of tests is large. The p-value score $sc_k$ as defined above takes values between 0 and 1.

At step S7, the results from the Analytical Modules M3 are stored in the Analytical results database D4. The Analytical Results database D4 consist of the analytical results obtained from the PCA and the p-value scores computed for the different categories defined in step S6.

At step S8, based on the data stored in Analytical results database D4, the Reporting modules M4 enable the creation of reports, tables and graphs that can be for interpretation in step S9. The Reporting Modules M4 can generate two types of tables, spreadsheet tables and report tables. The Reporting Module M4 has a built-in facility that enables semi-automatic generation of the report R1.

Figure 3:
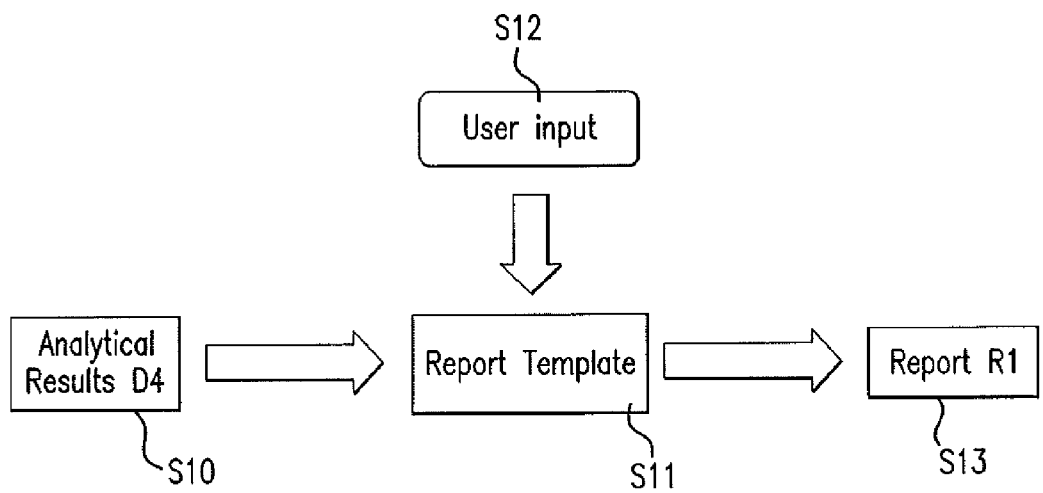
FIG. 3 is a process of report generation in accordance with the subject disclosure.

Referring now to FIG. 3, the process for generating a report is shown schematically. At step S10, the user calls the reporting function to generate analysis and a template file. At step S11, the template file contains all standard report sections, some of the tables R2 (described below) and some of the graphs R3 (described below). At step S12, the user edits the template file to add his or her interpretation in plain words before the report R1 is generated at step S13.

The Reporting Modules M4 generate two sets of tables R2. One type of table contains the p-value matrix. In the p-value matrix table, the columns are the tests and the rows the centers. The centers are sorted according to the rank of their p-value score so the top centers on the table are the most outlying. A second type of table is a summary table, as shown in FIG. 4. The summary tables are produced for each center providing detailed information about the abnormalities detected by the system and methods disclosed herein. The summary tables include the statistical tests results and show the aggregate number (i.e., mean, variance) for the center against the pooled aggregate numbers for all other centers. The summary tables enable the user to interpret the abnormalities and to pinpoint potentially problematic data.

The Reporting Modules M4 generate two sets of graphs R3. One type of graph, a frequency distribution of p-value scores, is shown in FIG. 5. In the graph of FIG. 5, centers that have a high p-value score are shown by a labeled vertical line. These centers are likely to contain problematic data. A second type of graph illustrates an individual factor map obtained from the PCA as shown in FIG. 6. In the graph of FIG. 6, each center is identified by a labeled point. Centers far from the origin behave differently from the bulk of centers around the origin and are likely to contain problematic data.

Central statistical monitoring can reveal data issues that had remained undiscovered after careful SDV and on-site checks. These data issues may in turn point to other problems, such as lack of resources or poor training at the data collection centers concerned, which would call for corrective actions. Central statistical monitoring allows highlighting problems, such as a lack of variability in blood pressure measurements or implausible values in a questionnaire, which would not have been detected by key risk indicator methods. This is because the former approach compares centers on all possible variables, while the latter approach focuses on specific, pre-defined variables of particular relevance to data quality. Targeted monitoring differs from central statistical monitoring in that it relies on "key risk indicators", the drawbacks of such an approach being the programming required for every new study, and the fact that not all data are exploited. In contrast, central statistical monitoring as described in this disclosure takes advantage of all the data and requires no trial-specific programming.

While the invention has been described with respect to preferred embodiments, those skilled in the art will readily appreciate that various changes and/or modifications can be made to the invention without departing from the spirit or scope of the invention. For example, each claim may depend from any or all claims, even in a multiple dependent manner, even though such has not been originally claimed. And, each step, module and component may be removed or rearranged in any sequence or combination.

What is claimed is:

1. A method for central monitoring of a research trial utilizing a plurality of distributed data collection centers, the method comprising the steps of:
creating and storing, in a network, a database consisting of datasets generated during the research trial;
preprocessing, by the network, the database to remove variables that are unsuitable for analysis;
extracting, by the network, metadata from the database to identify types of the variables;

storing, in the network, the preprocessed datasets and corresponding metadata in a statistical database that is in a format compatible for analysis;

executing statistical tests, in the network, on a data collection center by data collection center basis to detect abnormalities and patterns present in datasets of the statistical database;

creating and storing in the network a matrix containing p-values based upon the executed statistical tests, wherein the matrix has as many rows as there are data collection centers and as many columns as executed statistical tests;

identifying any outlying data collection centers by summarizing the p-values;

determining if any of the executed statistical tests are faulty and removing such faulty executed statistical tests from the matrix to create a filtered matrix, the elements of which are denoted $p_{ik}$; and computing an overall p-value score according to:

$$sc_k \exp\left(\frac{1}{qN_k}\sum_{i=1}^{qN_k} \log(p_{ik})\right)$$

where $N_k$ is the number of tests performed for center k, $p_{ik}$ are the sorted p-values for test i and center k, and q is a user-selected value between 0 and 1.

2. The method of claim 1, wherein the preprocessing step includes removing variables selected from the group consisting of: variables for which all observations are missing; variables for which all observations have the same value; variables for which the number of observations is too small; and technical variables.

3. The method of claim 1, wherein the extracting of metadata step includes deriving a number of visits per patient and creating a list of patients per center.

4. The method of claim 1, wherein the executing statistical tests step includes comparing each center to the other centers for each variable by fitting statistical models.

5. The method of claim 4, further comprising the step of deriving from the model aggregate numbers for each center.

6. The method of claim 4, wherein the aggregate numbers are selected from the group consisting of a mean, a variance; and a relevant estimator of a distribution characteristic of a variable for the respective center.

7. The method of claim 4, further comprising the step that from the model a probability can be assigned to each center, wherein the probability indicates a likelihood to draw a center more extreme than the corresponding center.

8. The method of claim 1, wherein the outlying center identification step analyzes a Principal Component Analysis of the p-values and a score method of the p-values.

9. A method for central monitoring of a research trial utilizing a plurality of distributed data collection centers, the method comprising the steps of:

preprocessing, by a network, a clinical database to remove variables that are unsuitable for analysis;

extracting metadata from the clinical database to identify types of the variables;

executing statistical tests in the network on data collection center by data collection center basis to detect abnormalities and patterns present in datasets of the statistical database, wherein the executing statistical tests step includes comparing each center to the other centers for each variable by fitting statistical models.

10. The method of claim 9, further comprising the step of creating and storing in a network a clinical database consisting of datasets generated during the research trial.

11. The method of claim 9, further comprising the step of storing in the network the preprocessed datasets and corresponding metadata in a statistical database that is in a format compatible for analysis.

12. The method of claim 9, further comprising the steps of:

creating and storing in the network a matrix containing p-values based upon the executed statistical tests, wherein the matrix has as many rows as there are data collection centers and as many columns as executed statistical tests;

identifying any outlying data collection centers by summarizing the p-values; and computing an overall p-value score according to:

$$sc_k \exp\left(\frac{1}{qN_k}\sum_{i=1}^{qN_k} \log(p_{ik})\right)$$

where $N_k$ is a number of tests for center k, $p_{ik}$ are a sorted p-values for the center k, and q is a user-selected value between 0 and 1.

13. The method of claim 9, further comprising the step of computing at least one sub-score selected from the group consisting of: (1) Tests on values based on distribution characteristics including at least one of a mean, a standard deviation, and proportion tests on categorical variables; (2) Tests on dates; (3) Tests on digits preference; and (4) Tests on underreporting including at least one of tests on missing values or tests on count of records.

14. The method of claim 12, wherein the preprocessing step includes removing variables selected from the group consisting of: variables for which all observations are missing; variables for which all observations have the same value; variables for which the number of observations is too small; and technical variables.

15. The method of claim 9, wherein the extracting of metadata step includes deriving a number of visits per patient and creating a list of patients per center.

16. The method of claim 9, further comprising the steps of deriving from the model aggregate numbers for each center.

17. The method of claim 9, wherein the aggregate number can be a mean, a variance or any relevant estimator of the distribution characteristic of a variable for the respective center.

18. The method of claim 9, further comprising the step that from the model, a probability is assigned to each center, wherein the probability indicates a likelihood to draw a center more extreme than the corresponding center.

* * * * *